US012729222B2

(12) United States Patent
Farber

(10) Patent No.: US 12,729,222 B2
(45) Date of Patent: Sep. 8, 2026

(54) ENHANCED PEPTIDE CONSTRUCTS FOR ALBUMIN BINDING

(71) Applicant: Michael Farber, Livingston, NJ (US)

(72) Inventor: Michael Farber, Livingston, NJ (US)

( * ) Notice: Subject to any disclaimer, the term of this patent is extended or adjusted under 35 U.S.C. 154(b) by 0 days.

(21) Appl. No.: 19/010,269

(22) Filed: Jan. 6, 2025

(65) Prior Publication Data

US 2026/0008820 A1 Jan. 8, 2026

Related U.S. Application Data

(63) Continuation-in-part of application No. 18/764,499, filed on Jul. 5, 2024, now abandoned.

(51) Int. Cl.
*A61K 39/395* (2006.01)
*C07K 14/00* (2006.01)

(52) U.S. Cl.
CPC ........ *C07K 14/001* (2013.01); *C07K 2319/70* (2013.01)

(58) Field of Classification Search
None
See application file for complete search history.

(56) References Cited

U.S. PATENT DOCUMENTS

2006/0228364 A1 10/2006 Dennis
2017/0233446 A1 8/2017 Glass

OTHER PUBLICATIONS

Rudikoff et al, PNAS vol. 79, p. 1979-1983 (Year: 1982).*
Dennis MS, Zhang M, Meng YG, Kadkhodayan M, Kirchhofer D, Combs D, Damico LA. Albumin binding as a general strategy for improving the pharmacokinetics of proteins. J Biol Chem. Sep. 2, 20020;277(38):35035-43. doi: 10.1074/jbc. M205854200. Epub Jul. 1, 20025. PMID: 12119302 [Date accessed: Jun. 18, 2024].
Zorzi A, Middendorp SJ, Wilbs J, Deyle K, Heinis C. Acylated heptapeptide binds albumin with high affinity and application as tag furnishes long-acting peptides. Nat Commun. Jul. 1, 20177;8:16092. doi: 10.1038/ncomms 16092. PMID: 28714475; Pmcid: PMC5520048 [Date accessed: Jun. 18, 2024].
Angelini A, Morales-Sanfrutos J, Diderich P, Chen S, Heinis C. Bicyclization and tethering to albumin yields long-acting peptide antagonists. J Med Chem. Nov. 2, 20126;55(22): 10187-97. doi: 10.1021/jm301276e. Epub Nov. 5, 2012. PMID: 23088498. [Date accessed: Jun. 18, 2024].
Michot, N et al. Albumin binding Nanofitins, a new scaffold to extend half-life of biologics -- a case study with exenatide peptide. Peptides vol. 152 (Jun. 2022) 170760. doi: 10.1016/j.peptides.2022. 170760 [Date accessed: Jun. 6, 2024].
KMD Bioscience Co. Ltd., Assay Report [Date accessed, Jul. 8, 2024].

* cited by examiner

*Primary Examiner* — Yunsoo Kim
(74) *Attorney, Agent, or Firm* — Michael J. Feigin, Esq.; Feigin and Fridman LLC.

(57) ABSTRACT

A synthetic peptide construct comprises an amino acid sequence-RLIEDICLPRWGCLWEDD (SEQ ID NO: 2) (also known as "GLYCLOK"), a flexible, hydrophilic glycine-serine (Gly-Ser) linker, and a polypeptide chain between 25 to 70 amino acids in length, which incorporates an albumin-binding moiety with a dissociation constant (Kd) to albumin of less than 20 nanomolar (nM). This construct may include the sequence RLIEDICLPRWGCLWEDD (SEQ. ID NO: 2) within its terminal 25 amino acids. The albumin-binding moiety may be cyclic, with a disulfide bond formed by at least one cysteine residue. The constructs is used as an agonist to modulate receptor interactions in vivo, enhancing therapeutic efficacy and extending circulating half-life in mammals, including humans. The peptides exhibit significant binding to albumin, enhancing bioavailability and therapeutic duration.

16 Claims, 1 Drawing Sheet

Specification includes a Sequence Listing.

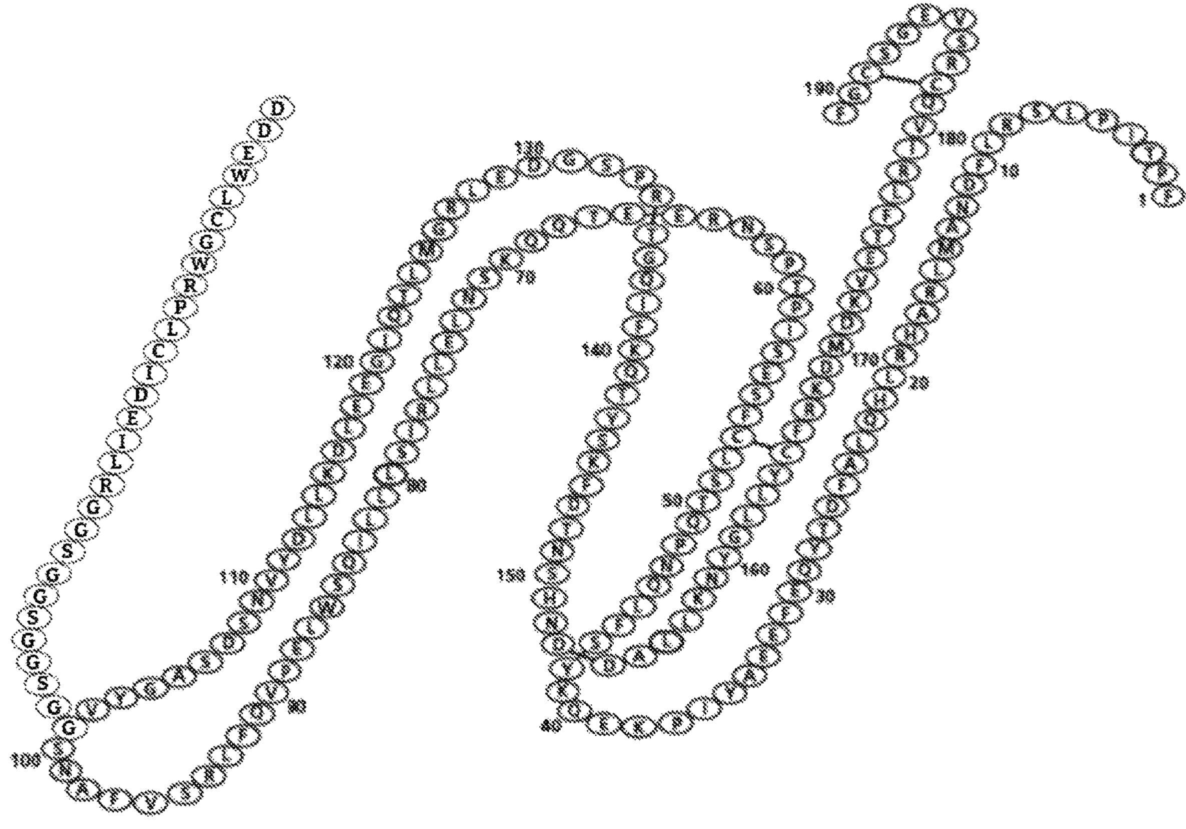

ENHANCED PEPTIDE CONSTRUCTS FOR ALBUMIN BINDING

REFERENCE TO SEQUENCE LISTING SUBMITTED ELECTRONICALLY

The contents of the electronic sequence listing (FBR010-SequenceListing.xml; Size: 2,215,449 bytes; and Date of Creation: Oct. 10, 2024) are herein incorporated by reference in their entirety.

FIELD OF THE DISCLOSED TECHNOLOGY

The disclosed technology relates to pharmacological and pharmaceutical drug delivery and proliferation. More specifically, the disclosed technology relates to a novel peptide construct that binds active proteins to circulating albumin in a subject.

BACKGROUND OF THE DISCLOSED TECHNOLOGY

Pharmaceutical research has focused on firstly enhancing the pharmacokinetics of therapeutic peptides and proteins in humans and mammals by binding them to albumin. Various methods like short peptide constructs, modified peptides, acylated peptides, Xtend additions, fusion to IgG or partial IgG moieties, PEGylation, and Nanofitin constructs have been employed for this purpose. Secondly these proteins are modified with unnatural proteins and related methods to slow or completely prevent enzymatic degradation of the peptide backbone. The combination of these two methods results in longer lived therapeutic peptides specifically designed to bind with high affinity to designated therapeutic receptors.

The above mentioned albumin binding technologies especially small peptide albumin binding constructs such as those described by Dennis et al 2002 still do not achieve the required level of albumin affinity to allow commercialization in human therapeutics and so there exists a need to discover novel small peptide albumin binding constructs with very low immunogenic potential and high albumin affinity across mammalian species.

Albumin, a key protein in plasma with a molecular mass of about 67 kDa and a half-life of 19 days in humans, plays a critical role in drug delivery. Peptide phage display technology has identified peptides containing the core sequence DICLPRWGCLW (SEQ ID NO: 1) that bind albumin with relatively high affinity at sites distinct from small molecule binding sites such as fatty acid binding sites. For instance, the peptide (Ac-RLIEDICLPRWGCLWEDD-NH2) (SEQ ID NO: 2) binds albumin with dissociation constants of 266±8 nM (rat), 320±22 nM (rabbit), and 467±47 nM (human), significantly extending half-lives when administered intravenously in rabbits as compared to therapeutic non albumin binding constructs.

Fusions of albumin-binding peptides such as described by Dennis et al 2002 with therapeutic proteins, such as the anti-tissue factor Fab of D3H44, have shown enhanced pharmacokinetics with prolonged half-lives in animal models, surpassing traditional strategies. These advancements, coupled with protein fusions, glycosylation, and PEGylation techniques, demonstrate the potential to optimize drug exposure by leveraging albumin's natural carrier function.

SUMMARY OF THE DISCLOSED TECHNOLOGY

Novel albumin binding constructs enhance the pharmacokinetic performance of therapeutic peptides and proteins, lengthening half lives thereof in the body and reducing necessary administering of drugs to furtherly spaced increments. Central to these constructs is an amino acid sequence incorporating the core peptide DICLPRWGCLW (SEQ ID NO: 1), covalently linked to hydrophilic and flexible glycine-serine series as example ggsggsggsgg (SEQ ID NO: 3). These linkers of format (ggs)Xgg (SEQ ID NO: 11), where X is 3 to 8 in some embodiments, facilitate unexpected robust binding affinity to albumin, characterized by a binding dissociation constant of less than 30 nanomolar to human albumin in therapeutic peptide constructs. Some instances of the constructs may feature the RLIEDICLPRWGCLWEDD (SEQ ID NO: 2) peptide as a foundational element, with the preferred ggsggsggsgg (SEQ ID NO: 3) linker strategically attached to one end, producing the novel albumin binding construct ggsggsggsggRLIEDICLPRWGCLWEDD (SEQ ID NO: 4). It is hypothesized that the specific ggs linker moiety ensures both flexibility and hydrophilicity critical for effective albumin interaction. Some embodiments of these constructs may allow for the fusion of active proteins, such as glp1 analogues 1 which can be covalently bound to the ggsggsggsggRLIEDICLPRWGCLWEDD (SEQ ID NO: 4) and the final construct then non-covalently associates with albumin thus achieving extended half-life in circulation.

Embodiments of the disclosed technology can be partially assembled using cellular protein expression methodologies, including systems such Transgenic Insect Cells, and plasmid-modified prokaryotic bacterium such as *E. coli* (*Escherichia coli*) plus synthetic methods to add unnatural amino acids lengths and the cyclized ggsggsggsggRLIEDICLPRWGCLWEDD (SEQ ID NO: 4) which is attached at either terminal or along the peptide backbone of the therapeutic peptide in such a manner as to maximize albumin binding and maximize the therapeutic peptide interaction with the intended receptor or receptors. Additionally, to ensure scalability and efficiency in production of the peptide constructs, chemical synthetic methods of assembly may be utilized. A peptide construct, protein, or other bio-molecule assembled outside a living organism is said to be "synthetic." Synthetic methods of assembly include ell-free protein synthesis (CFPS) and in-vitro peptide synthesis. A "peptide construct" comprises at least two amino acids bound to one another.

Upon administration into mammalian or avian subjects, the albumin binding constructs may exhibit a prolonged half-life comparable to at least 90% of the native albumin half-life in the respective species. Specific embodiments targeting glp1 analogues demonstrate a binding dissociation coefficient to GLP1R within the range of 5 to 30 nanomolar in line with their theoretical values, with optimized constructs achieving a coefficient of about 8.9 nanomolar binding to the GLP1 receptor. These constructs show high affinity for mammalian albumin in the 20 nM range and below. Importantly, these constructs may be designed to minimize antigenicity when administered in vivo, ensuring compatibility and safety for therapeutic applications aimed at improving drug delivery efficacy and patient outcomes.

BRIEF DESCRIPTION OF THE DRAWINGS

FIG. 1 shows a growth hormone agonist (SEQ ID NO: 12) in an embodiment of the disclosed technology. Each circle is an amino acid.

DETAILED DESCRIPTION OF EMBODIMENTS OF THE DISCLOSED TECHNOLOGY

A synthetic peptide construct has an amino acid sequence of RLIEDICLPRWGCLWEDD (SEQ ID NO: 2), a flexible and hydrophilic glycine-serine (Gly-Ser) linker of format (ggs)Xgg (SEQ ID NO: 11) where X is from 3 to 8 and covalently linked to a polypeptide chain of between 5 to 200 amino acids in length, and an albumin-binding moiety with a dissociation constant (Kd) to human albumin of less than 30 nanomolar (nM). This construct may include, within its terminal 25 amino acids, the sequence RLIEDICL-PRWGCLWEDD (SEQ ID NO: 2) where a thiol group of at least one cysteine forms a disulfide bond, thereby cyclizing the cysteines. For purposes of this disclosure a technology comprising a synthetic molecule can be referred to as "synthetic" despite the presence of non-synthetic components if the component has at least one synthetically synthesized amino acid. For example, a peptide having amino acid synthesized ex-vivo by chemical processes executed externally to a living organism is considered to be a "synthetic peptide".

In embodiments such as when the disclosed technology is used with a "semaglutide" analogue, amino acids 7 and 8 may be chemically attached following the expression of peptides 9 to 37 (or 38) as recombinant proteins in *E. coli* or through chemical synthesis. For purposes of this disclosure, a terminal amino acid along a peptide chain is assigned a numerical locant of 1, with each subsequent amino acid along the chain having a locant with a numerical value 1 greater than the previous locant. For example, in RLIEDI-CLPRWGCLWEDD (SEQ ID NO: 2), the first R has a locant of 1, the subsequent L has a locant of 2, the adjacent I a locant of 3, etc.

The described technology may interact with biochemical pathways in a subject after administration via injection into the blood stream (and/or other methods) agonistically. More specifically, the protein bound to the construct or constituting a component of the construct may interact with bodily receptors in a signalling pathway, thereby inducing a biochemical effect, which can be modulated by the concentration, volume, and frequency of administering. Some embodiments may be dual-agonists, meaning that they target and activate two biochemical pathways simultaneously, while other embodiments be tri-agonists.

In an embodiment of the disclosed technology, the GLP-1 construct GMT 60 includes cysteines in the albumin binding construct hereinafter referred to as GLYCLOK (ggsggsggsg-gRLIEDICLPRWGCLWEDD) (SEQ ID NO: 4) forming a disulfide bond between jts cysteines, GLP-1 analogue from amino acids 7 to 37, and GLYCLOK attached at the N-terminus. A specific example sequence of said novel semaglutide like construct is:

```
                                        (SEQ ID NO: 5)
H-Aib-EGTFTSDVSSYLEGQAAK
EFIAWLVRGRGG-GGSGGSGGSGGRLIEDICLPRWGCLWEDD
```

This peptide has an in vivo half-life in canines ranging from 6 to 8 days.

A dual GLP-1/GIP agonist synthetic peptide may incorporate two unnatural amino acids (Aib) at positions 2 and 13, with position 20 allowing for attachment of GLYCLOK via any suitable amino acid preferably glutamic acid. An example sequence for this peptide is:

```
                                        (SEQ ID NO: 6)
Y-Aib-EGTFTSDYSIAiB-LDKIAQXAFVQWLIAGGPSSGAPPPS.
```

(X represents the attachment point for GLYCLOK.)

Another dual GLP-1/GIP agonist example features the sequence:

```
                                        (SEQ ID NO: 13)
Y-Aib-EGTFTSDYSIAiB-GXAFVGWLIAGGPSSGAPPPS-NH2.
```

(X again denotes the attachment point for GLYCLOK being any suitable amino acid preferably glutamic acid).

A dual amylin/calcitonin receptor agonist may feature the sequence: GRGRVLWAIFXAAQGELYSSVDSTFTGEH-NH2 (SEQ ID NO: 7). (GLYCLOK attaches at position 11 or 19, with X indicating a glutamic acid or other suitable amino acid glutamic acid being a preferred substitution.)

A dual GLP-1/secretin agonist may use the sequence: H-Aib-EGTFTSDVSYLXEEAiB-LQRFLEHLV (SEQ ID NO: 8). (X represents a suitable amino acid preferably glutamic acid for GLYCLOK attachment.)

A triagonist (GLP-1/GIP/glucagon) semisynthetic peptide, as described in EP306617B1, may include the sequence: Y-Aib-QGFTFSDYSIYLEKXAAKEFVEWLL-SAGPPSGAPPPS (SEQ ID NO: 9). (X indicates a suitable amino acid where glutamic acid is a preferred amino for GLYCLOK attachment.)

An NKR agonist synthetic peptide may comprise the sequence: DDEWLCGRPLCIDEILRggsggsggsgg-Lys-Phe-Val-Gly-N-MethylLeucine-NorLeucine-NH2 (SEQ ID NO: 10). (GLYCLOK attaches to a terminal or non-terminal amino acid, preferably glycine or serine at terminal and preferably glutamic acid at non terminal.)

A growth hormone agonist may feature 190 amino acids and two disulfide bridges, with GLYCLOK attaching at positions 100 or 101 via suitable amino acid preferably glutamic acid.

FIG. 1 shows a growth hormone agonist in an embodiment of the disclosed technology. A growth hormone agonist may feature 190 amino acids and two disulfide bridges, with GLYCLOK attaching at positions 100 or 101 via glutamic acid. Amino acid adjoined to 100 constitutes the first amino acid of the GLYCLOK albumin binder which has the structure GGSGGSGGSGGRLIEDICLPRWGCLWEDD (SEQ ID NO: 4). The amino acids C and C at positions 53 and 165 respectively share a disulfide bond, as do the C at position 182 and the C at position 189.

Semisynthetic peptides of this type may be combined synergistically with other drugs or among themselves to treat, alleviate, or cure ailments in mammals, including humans. These peptides may exhibit SPR (Surface Plasmon Resonance) dissociation binding constants to mammalian albumins of <100 nM, <50 nM, and/or <30 nM. The half-life of embodiments of the synthetic peptide constructs in humans ranging from 18 to 21 days, based on in vivo pharmacokinetics.

An albumin binding construct comprises an amino acid sequence centered around the core peptide DICL-PRWGCLW (SEQ ID NO: 1). This core peptide is covalently bound to at least one glycine-serine (Gly-Ser) linker of the format (ggs)Xgg (SEQ ID NO: 11) where X is 3 to 8, these linkers possessing hydrophilicity and flexibility. The inclusion of these specific Gly-Ser linkers not only enhances the flexibility and solubility of the constructs but also significantly improves its binding affinity to Mammalian albumins wherein the core peptides showed affinities of approximately 500 nM or more by SPR analysis to human albumin. This unprecedented high affinity of the novel albumin binding construct is quantified by an unprecedentedly low binding dissociation constant (Kd) value of less than 30 nanomolar to human albumin as measured by SPR, indicating a strong and stable interaction with albumin, thus ensuring that the therapeutic peptides and proteins maintain extended half-lives in the circulatory system, thereby enhancing therapeutic efficacy.

We hypothesize that when the linker is sufficiently modified to be flexible and hydrophilic, the binding affinity is, in embodiments, increased 100-fold. The albumin binder may be constructed synthetically, as a synthetic element produced in-vitro, ex-vivo, and/or cell-free protein synthesis before being attached to a protein. The binder, also referred to as an "albumin binding moiety", binds to albumin whilst bio-chemical characteristics of proteins to which the binder is additionally bound are substantially maintained. Described differently, the albumin binding moiety adjoins a target protein and/or bio-chemical agent such as a drug to blood-borne albumin, thereby enabling the target protein/agent to circulate within the bloodstream. This approach is highly effective in distributing target agents throughout the body whilst maintaining their solubility to maximize bioavailability. To preserve normal albumin function, concentration, and recycling in the body, the albumin-binding moiety may bind to albumin at a binding site of albumin farthest from the fetal receptor (FcRn) binding site of albumin.

Naturally occurring glycine-serine linkers of the format (ggs)Xgg (SEQ ID NO: 11) where X is 3 to 8 are highly hydrophilic and flexible within three-dimensional space, enabling proteins, enzymes, substrates, and other biochemical compounds to assume various orientations. This property of the specific linkers allows for unexpectedly low binding dissociation constants (less than 20 nanomolar) with human albumin of the preferred constructs using ggsggsggsggRLIEDICLPRWGCLWEDD (SEQ ID NO: 4). For purposes of this disclosure, a biomolecule is said to be "naturally occurring" if said biomolecule is found in living organisms without artificial intervention or insertion.

A Glycine-Serine (Gly-Ser) linker is a sequence of amino acids comprised of repeating units of glycine and serine amino acids. Glycine, being the smallest amino acid with a hydrogen as its side chain, provides minimal steric hindrance and high flexibility, while serine, with a hydroxyl group, contributes to the linker's hydrophilicity, allowing for effective interaction with aqueous environments.

Albumin is a main protein of blood plasma, maintaining the oncotic pressure necessary for proper distribution of body fluids between body tissues and the bloodstream. It also serves as a carrier protein for various substances, including hormones, vitamins, and drugs. The binding constructs thus target albumin for binding, as it can circulate active proteins bound thereto to organs, tissues, and cells throughout the body. A biomolecule is said to be "active" if it is in a conformation with which it can perform its typical function. Thus, a denatured protein is not said to be active.

The binding dissociation constant (Kd) is a measure of the affinity between two binding partners, such as a peptide and albumin. A lower Kd value indicates a higher affinity, meaning the peptide binds more strongly to albumin. In this context, a Kd of less than 20 nanomolar (nM) indicates strong binding.

Common amino acids found in embodiments of the disclosed technology are: Alanine (Ala or A), Arginine (Arg or R), Asparagine (Asn or N), Aspartic Acid (Asp or D), Cysteine (Cys or C), Glutamine (Gln or Q), Glutamic Acid (Glu or E), Glycine (Gly or G), Histidine (His or H), Isoleucine (Ile or I), Leucine (Leu or L), Lysine (Lys or K), Methionine (Met or M), Phenylalanine (Phe or F), Proline (Pro or P), Serine (Ser or S), Threonine (Thr or T), Tryptophan (Trp or W), Tyrosine (Tyr or Y), and Valine (Val or V). It should be understood that the full name, as well as the three-letter and one-letter abbreviations for each respective amino acids refer to the same molecular structure, and may be used interchangeably. Additionally, the synthetic amino acid α-aminoisobutyric acid may be referred to as "Aib".

Albumin binding constructs in embodiments of the disclosed technology comprise a core peptide DICLPRWGCLW (SEQ ID NO: 1). The core peptide, in some embodiments, is part of a larger peptide RLIEDICLPRWGCLWEDD (SEQ ID NO: 2), comprising a distal end followed by an 11-glycine-serine linker this preferred albumin binding construct being ggsggsggsggRLIEDICLPRWGCLWEDD (SEQ ID NO: 4). This glp1 analogue structure shows significant binding to human albumin at 28.9 nanomolar and also binds to GLP1R at a rate of 8.9 nanomolar as predicted by literature and thus similar to its acylated counterparts. Using this peptide, binding efficiency to albumin is improved, thereby lengthening the half lives of active proteins bound thereto.

The disclosed technology, in some embodiments, is used with other proteins, such as GLP-1 (glucagon-like peptide-1) used in anti-obesity treatments. Active proteins bound to GLYCLOK constructs can circulate in the body for a month having a half life of approximately 18 to 20 days, as opposed to current acylated pharmaceuticals of the GLP-1 class typically have half lives in the range of 4 to 7 days thus needing injections in the body after a week. The novel binder disclosed herein used in the GLP-1 analogue agonist, confers a dissociation constant of 28 nM of the novel GLP-1 construct for human serum albumin. As. shown in the original patent by Dennis and the associated publications by him of the SA21 (RLIEDICLPRWGCLWEDD) (SEQ ID NO: 2) binder without use of the disclosed technology shows dissociation constants of approximately 500 nM with human serum albumin.

The constructs are effective across various mammalian species, including rats, rabbits, horses, felines, canines, and humans.

The constructs are typically produced by cellular protein expression and synthetic methods wherein a plasmid DNA fragment coding for some components of the construct are integrated into the genome of a target cell. Such target cells may be Transgenic Insect Cells or *E coli* cells expressing the segment comprising natural amino acids. *E. coli* cells can be advantageously combined with chemical synthetic methods disclosed herein.

The constructs can then be attached to active three-dimensional proteins, such as growth hormone, without compromising the activity of the three-dimensional protein or its binding activities to substrates. The disclosed technology is significantly less antigenic than albumin-binding technologies disclosed in prior art, thereby increasing safety for clinical use and mitigating concern of immunogenic response due to large, globular, and foreign entrants into the circulatory system.

In an embodiment of the disclosed technology, a partially synthesized construct is a novel GLP-1 analogue agonist that, formed from amino acids 9 through 36 plus ggsggsggsggRLIEDICLPRWGCLWEDD (SEQ ID NO: 4) peptide at the C terminal, is produced by a recombinant protein expression in *E. coli* of aminos 9 through 36, where the amino acids 7 and 8 are chemically added to this construct of such that the complete protein is functional with an albumin binding constant of 0.29 nM (nanomolar) and a GLP-1 receptor binding constant of 8.9 nM.

The necessity of utilizing chemical synthesis in the protein of this embodiment is required due to amino acid 8 being 2-aminoisobutyric acid which is a rare, non-protein amino acid. While in this embodiment both in-vivo and in-vitro syntheses are employed for different components of the construct, other embodiments may be assembled entirely synthetically.

Any device or step to a method described in this disclosure can comprise or consist of that which it is a part of, or the parts which make up the device or step. The term "and/or" is inclusive of the items which it joins linguistically and each item by itself. "Substantially" is defined as at least 95% of the term being described and/or "within a tolerance level known in the art and/or within 5% thereof. Any device or aspect of a device or method described herein can be read as "comprising" or "consisting" thereof.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

I claim:

1. A synthetic peptide construct comprising:

a polypeptide chain between 5 to 200 amino acids in length, inclusive, said polypeptide chain having the internal amino acid or branched sequence or terminal sequence including DICLPRWGCLW (SEQ ID NO: 1) as part of a novel albumin binding moiety covalently bound to said polypeptide chain, said albumin binding moiety comprising a flexible and hydrophilic glycine-serine (Gly-Ser) linker of SEQ ID NO: 5, having a binding dissociation constant (Kd) to human-albumin of less than 30 nanomolar (nM).

2. The synthetic peptide construct of claim 1, wherein:

a thiol group of at least one cysteine amino acid forms a disulfide bond, such that said cysteines are cyclized.

3. The synthetic peptide construct of claim 1, wherein said synthetic polypeptide has a half life of at least 6 days in canines.

4. The synthetic peptide construct of claim 1, wherein said synthetic polypeptide acts agonistically or antagonistically in a biochemical pathway upon administering to a living subject.

5. The synthetic polypeptide construct of claim 1, wherein said synthetic polypeptide acts as a dual glp1/gip agonist in humans.

6. The synthetic peptide construct of claim 5, wherein said polypeptide chain comprises two synthetic Aib (α-aminoisobutyric acid) molecules.

7. The synthetic peptide construct of claim 1, wherein said synthetic polypeptide acts as a dual amylin/calcitonin receptor agonist in humans or other mammals.

8. The synthetic peptide construct of claim 1, wherein said synthetic polypeptide acts as a triagonist of glp1/gip/glucagon in humans.

9. The synthetic peptide construct of claim 1, wherein said synthetic peptide construct acts as a NKR agonist in humans.

10. The synthetic peptide construct of claim 9, wherein said synthetic peptide construct acts as a NK2R agonist in humans the peptide structures.

11. The synthetic peptide construct of claim 1, wherein said synthetic peptide construct acts as a growth hormone agonist in humans.

12. The synthetic peptide construct of claim 1 having an SPR dissociation binding constant to a mammalian albumin of less than 100 nM.

13. The synthetic peptide construct of claim 1 having an SPR dissociation binding constant to a mammalian albumin of less than 50 nM.

14. The synthetic peptide construct of claim 1 having an SPR dissociation binding constant to a mammalian albumin of less than 30 nM.

15. The synthetic peptide construct of claim 4 having a half life in humans of at least 18 days.

16. The synthetic peptide construct of claim 1, wherein said albumin binding moiety binds to albumin at a binding site of albumin furthest from the FcRN binding site.

* * * * *

SEQUENCE LISTING

```
Sequence total quantity: 13
SEQ ID NO: 1            moltype = AA  length = 11
FEATURE                 Location/Qualifiers
source                  1..11
                        mol_type = protein
                        organism = synthetic construct
SEQUENCE: 1
DICLPRWGCL W                                                    11

SEQ ID NO: 2            moltype = AA  length = 18
FEATURE                 Location/Qualifiers
source                  1..18
                        mol_type = protein
                        organism = synthetic construct
SEQUENCE: 2
RLIEDICLPR WGCLWEDD                                             18

SEQ ID NO: 3            moltype = AA  length = 11
FEATURE                 Location/Qualifiers
source                  1..11
                        mol_type = protein
                        organism = synthetic construct
SEQUENCE: 3
GGSGGSGGSG G                                                    11

SEQ ID NO: 4            moltype = AA  length = 29
FEATURE                 Location/Qualifiers
source                  1..29
                        mol_type = protein
                        organism = synthetic construct
SEQUENCE: 4
GGSGGSGGSG GRLIEDICLP RWGCLWEDD                                 29

SEQ ID NO: 5            moltype = AA  length = 61
FEATURE                 Location/Qualifiers
source                  1..61
                        mol_type = protein
                        organism = synthetic construct
MOD_RES                 2
                        note = Aib
SEQUENCE: 5
HXEGTFTSDV SSYLEGQAAK EFIAWLVRGR GGGGSGGSGG SGGRLIEDIC LPRWGCLWED  60
D                                                               61

SEQ ID NO: 6            moltype = AA  length = 39
FEATURE                 Location/Qualifiers
source                  1..39
                        mol_type = protein
                        organism = Synthetic construct
MOD_RES                 2
                        note = Aib
MOD_RES                 13
                        note = Aib
VARIANT                 20
                        note = any amino acid, preferably glutamic acid
SEQUENCE: 6
YXEGTFTSDY SIXLDKIAQX AFVQWLIAGG PSSGAPPPS                      39

SEQ ID NO: 7            moltype = AA  length = 29
FEATURE                 Location/Qualifiers
```

-continued

```
source                  1..29
                        mol_type = protein
                        organism = synthetic construct
VARIANT                 11
                        note = any amino acid, preferably glutamic acid
SEQUENCE: 7
GRGRVLWAIF XAAQGELYSS VDSTFTGEH                                    29

SEQ ID NO: 8            moltype = AA  length = 28
FEATURE                 Location/Qualifiers
source                  1..28
                        mol_type = protein
                        organism = synthetic construct
MOD_RES                 2
                        note = Aib
VARIANT                 14
                        note = any amino acid, preferably glutamic acid
SEQUENCE: 8
HXEGTFTSDV SYLXEEAIBL QRFLEHLV                                     28

SEQ ID NO: 9            moltype = AA  length = 39
FEATURE                 Location/Qualifiers
source                  1..39
                        mol_type = protein
                        organism = synthetic construct
MOD_RES                 2
                        note = Aib
VARIANT                 17
                        note = any amino acid, preferably glutamic acid
SEQUENCE: 9
YXQGFTFSDY SIYLEKXAAK EFVEWLLSAG PPSGAPPPS                         39

SEQ ID NO: 10           moltype = AA  length = 34
FEATURE                 Location/Qualifiers
source                  1..34
                        mol_type = protein
                        organism = synthetic construct
MOD_RES                 33
                        note = N-MethylLeucine
MOD_RES                 34
                        note = Nle
SEQUENCE: 10
DDEWLCGRPL CIDEILRGGS GGSGGSGGKF VGXX                              34

SEQ ID NO: 11           moltype = AA  length = 13
FEATURE                 Location/Qualifiers
source                  1..13
                        mol_type = protein
                        organism = synthetic construct
VARIANT                 4..11
                        note = where X is 3 to 8 and X represents any amino acid
SEQUENCE: 11
GGSXXXXXXX XGG                                                     13

SEQ ID NO: 12           moltype = AA  length = 190
FEATURE                 Location/Qualifiers
source                  1..190
                        mol_type = protein
                        organism = synthetic construct
SITE                    100..101
                        note = The terminal G of Seq ID #4 is bound between the S
                         at 100 and the V at 101
SEQUENCE: 12
FPTIPLSRLF DNAMLRAHRL HQLAFDTYQE FEEAYIPKEQ KYSFLQNPQT SLCFSESIPT  60
PSNREETQQK SNLELLRISL LLIQSWLEPV QFLRSVFANS VYGASDSNVY DLLKDLEEGI  120
QTLMGRLEDG SPRTGQIFKQ TYSKFDTNSH NDDALLKNYG LLYCFRKDMD KVETFLRIVQ  180
CRSVEGSCGF                                                         190

SEQ ID NO: 13           moltype = AA  length = 36
FEATURE                 Location/Qualifiers
source                  1..36
                        mol_type = protein
                        organism = Synthetic construct
MOD_RES                 2
                        note = Aib
MOD_RES                 13
                        note = Aib
```

-continued

```
VARIANT                 15
                        note = any amino acid, preferably glutamic acid
SEQUENCE: 13
YXEGTFTSDY SIXGXAFVGW LIAGGPSSGA PPPSNH                         36
```